United States Patent
Armstrong

(10) Patent No.: US 8,190,258 B2
(45) Date of Patent: *May 29, 2012

(54) LEAD CONDITION ASSESSMENT FOR AN IMPLANTABLE MEDICAL DEVICE

(75) Inventor: Randolph K. Armstrong, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 179 days.

This patent is subject to a terminal disclaimer.

(21) Appl. No.: 12/499,001

(22) Filed: Jul. 7, 2009

(65) Prior Publication Data
US 2009/0270959 A1    Oct. 29, 2009

Related U.S. Application Data

(63) Continuation of application No. 11/262,243, filed on Oct. 28, 2005, now Pat. No. 7,567,840.

(51) Int. Cl.
*A61N 1/37* (2006.01)
(52) U.S. Cl. ............................... 607/27; 607/28
(58) Field of Classification Search ............... 607/27–29
See application file for complete search history.

(56) References Cited

U.S. PATENT DOCUMENTS

| | | |
|---|---|---|
| 3,796,221 A | 3/1974 | Hagfors |
| 4,291,699 A | 9/1981 | Geddes et al. |
| 4,573,481 A | 3/1986 | Bullara |
| 4,606,349 A | 8/1986 | Livingston et al. |
| 4,630,615 A | 12/1986 | Yomtov |
| 4,850,356 A | 7/1989 | Heath |
| 4,867,164 A | 9/1989 | Zabara |
| 4,870,341 A | 9/1989 | Pihl et al. |
| 4,899,750 A | 2/1990 | Ekwall |
| 4,964,407 A | 10/1990 | Baker, Jr. et al. |
| 5,137,020 A | 8/1992 | Wayne et al. |
| 5,137,021 A | 8/1992 | Wayne et al. |
| 5,146,920 A | 9/1992 | Yuuchi et al. |
| 5,154,172 A | 10/1992 | Terry, Jr. et al. |

(Continued)

FOREIGN PATENT DOCUMENTS
WO    2004075982 A1    9/2004

OTHER PUBLICATIONS

Terry, R.S. et al.; "The Implantable Neurocybemetic Prosthesis System," Pacing and Clinical Electrophysiology, vol. 14, No. 1 (Jan. 1991), pp. 86-93.

*Primary Examiner* — Carl H Layno
*Assistant Examiner* — Jessica Sarcione
(74) *Attorney, Agent, or Firm* — Cyberonics, Inc.

(57) ABSTRACT

A method, system, and apparatus for performing a lead condition assessment and/or a lead orientation determination associated with an implantable medical device (IMD). A first impedance is determined. The first impedance relates to the impedance relative to a first electrode and a portion of the IMD. A second impedance is determined. The second impedance relates to the impedance relative to a second electrode and the portion of the IMD. The first impedance is compared with the second impedance to determine an impedance difference. A determination is made whether the impedance difference is outside a predetermined tolerance range. Furthermore, artifact measured during impedance measurements or test pulses may be compared to assess lead orientation. An indication of a lead condition error is provided in response to determining that the impedance difference is outside the predetermined tolerance range.

20 Claims, 10 Drawing Sheets

U.S. PATENT DOCUMENTS

| | | |
|---|---|---|
| 5,179,950 A | 1/1993 | Stanislaw |
| 5,201,808 A | 4/1993 | Steinhaus et al. |
| 5,201,865 A | 4/1993 | Kuehn |
| 5,222,494 A | 6/1993 | Baker, Jr. |
| 5,237,991 A | 8/1993 | Baker, Jr. et al. |
| 5,431,692 A | 7/1995 | Hansen et al. |
| 5,501,702 A | 3/1996 | Plicchi et al. |
| 5,507,786 A | 4/1996 | Morgan et al. |
| 5,522,865 A | 6/1996 | Schulman et al. |
| 5,534,018 A | 7/1996 | Wahlstrand et al. |
| 5,549,646 A | 8/1996 | Katz et al. |
| 5,620,474 A | 4/1997 | Koopman |
| 5,741,311 A | 4/1998 | Mc Venes et al. |
| 5,755,742 A | 5/1998 | Schuelke et al. |
| 5,814,088 A | 9/1998 | Paul et al. |
| 5,876,425 A | 3/1999 | Gord et al. |
| 5,891,179 A | 4/1999 | Er et al. |
| 5,897,577 A | 4/1999 | Cinbis et al. |
| 6,073,050 A | 6/2000 | Griffith |
| 6,181,969 B1 | 1/2001 | Gord |
| 6,212,431 B1 | 4/2001 | Hahn et al. |
| 6,216,045 B1 | 4/2001 | Black et al. |
| 6,317,633 B1 | 11/2001 | Jorgenson et al. |
| 6,400,988 B1 | 6/2002 | Gurewitsch |
| 6,418,348 B1 | 7/2002 | Witte |
| 6,445,951 B1 | 9/2002 | Mouchawar |
| 6,453,198 B1 | 9/2002 | Torgerson et al. |
| 6,490,486 B1 | 12/2002 | Bradley |
| 6,510,332 B1 | 1/2003 | Greenstein |
| 6,553,263 B1 | 4/2003 | Meadows et al. |
| 6,620,186 B2 | 9/2003 | Saphon et al. |
| 6,648,823 B2 | 11/2003 | Thompson |
| 6,658,294 B1 | 12/2003 | Zadeh et al. |
| 7,567,840 B2 * | 7/2009 | Armstrong ............... 607/27 |
| 2002/0143368 A1 | 10/2002 | Bakels et al. |
| 2002/0153901 A1 | 10/2002 | Davis et al. |
| 2003/0139781 A1 * | 7/2003 | Bradley et al. ............ 607/48 |
| 2005/0177206 A1 | 8/2005 | North et al. |
| 2005/0272280 A1 | 12/2005 | Osypka |

* cited by examiner

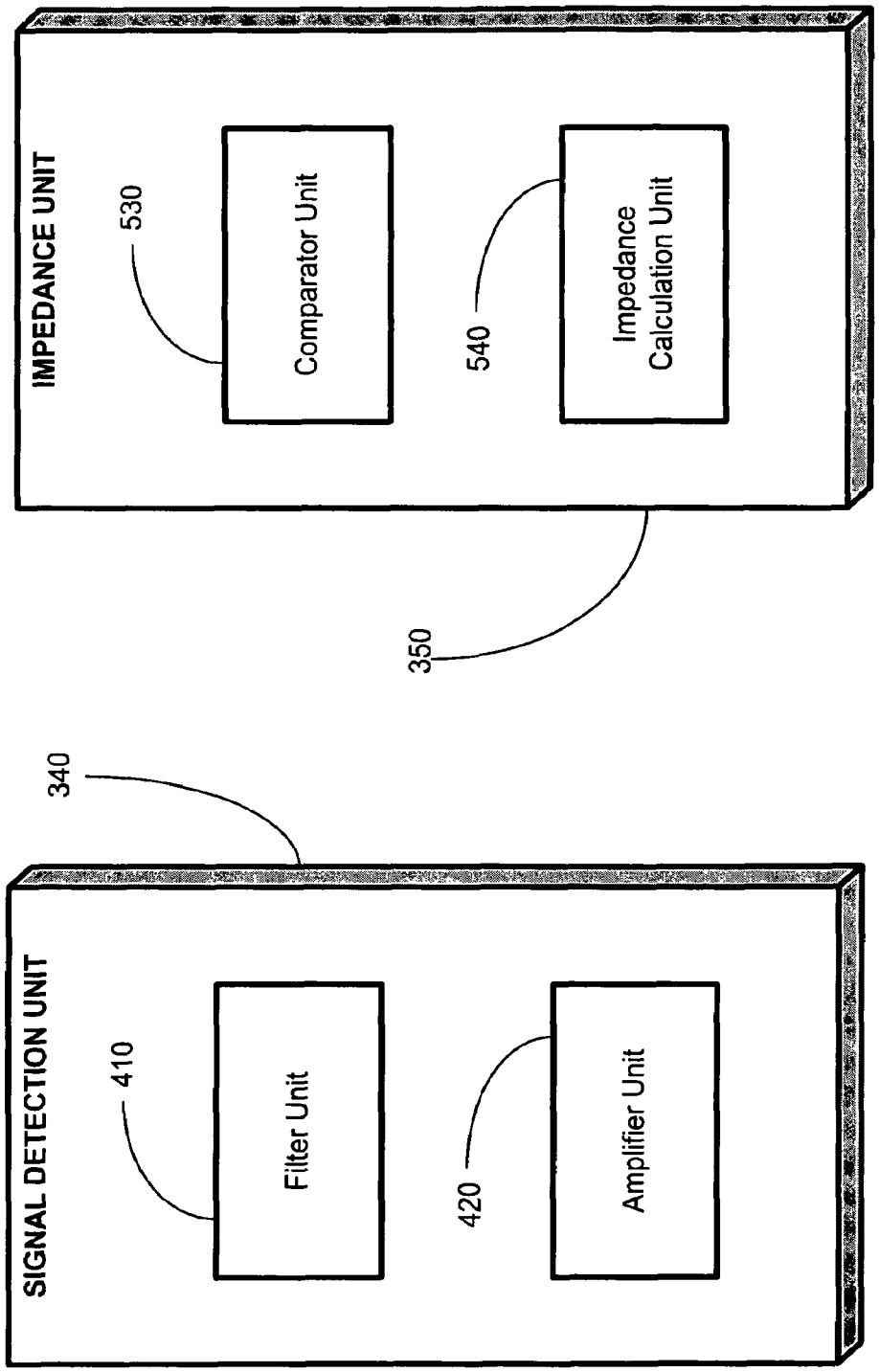

LEAD CONDITION ASSESSMENT FOR AN IMPLANTABLE MEDICAL DEVICE

CROSS-REFERENCE TO RELATED APPLICATION

This is a continuation of U.S. application Ser. No. 11/262,243 (the '243 application), entitled "LEAD CONDITION ASSESSMENT FOR AN IMPLANTABLE MEDICAL DEVICE", filed Oct. 28, 2005, in the name of the inventor, Randolph K. Armstrong, now U.S. Pat. No. 7,567,840. The earlier effective filing date of the '243 application is hereby claimed under 35 U.S.C. §120. The '243 application is hereby incorporated by reference in its entirety for all purposes as if expressly set forth verbatim herein.

BACKGROUND OF THE INVENTION

1. Field of the Invention

This invention relates generally to implantable medical devices, and, more particularly, to methods, apparatus, and systems for providing an assessment relating to the condition of a lead coupled to the implantable medical device.

2. Description of the Related Art

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. No. 4,702,254 to Dr. Jacob Zabara, which is hereby incorporated in its entirety herein by reference in this specification. Electrical stimulation of the vagus nerve (hereinafter referred to as vagus nerve stimulation therapy or VNS) may be provided by implanting an electrical device underneath the skin of a patient and performing a detection and electrical stimulation process. Alternatively, the system may operate without a detection system once the patient has been diagnosed with epilepsy, and may periodically apply a series of electrical signals to the vagus (or other cranial) nerve intermittently throughout the day, or over another predetermined time interval.

Generally, therapeutic electrical stimulation is delivered by the implantable device via a lead, which is coupled to one or more electrodes coupled, in turn, to a target location of the patient's body. A plurality of electrodes that are associated with an implantable medical device are generally operatively connected to the implantable device via individual leads. A number of leads may project from the implantable device onto various portions of a patient's body. For example, a number of electrodes may be attached to various points of a nerve or other tissue inside a human body. Occasionally, problems with the lead and/or electrodes may occur. These problems may include a malfunction or damage of the lead and/or electrode, or a change in the tissue surrounding the implanted lead and/or electrode.

Often, various electrodes are implanted in contact with target portions of the human body, such as a vagus nerve, in order to deliver electrical signals to provide therapy or to monitor signals. Subsequent to the implanting of the implantable device, the associated leads, electrodes and/or connections between the electrodes and the implantable device may deteriorate over time. Additionally, changes in the tissue surrounding the lead and/or electrodes may cause electrical variations experienced by the implantable device system, which may affect the operation of the leads and electrodes themselves. Electrical characteristics associated with the leads and electrodes carrying the stimulation signal or monitored signal may deteriorate over time, thereby altering the operation of the implantable device. Furthermore, physiologic changes in the human body may also affect the operation of the implantable device since these changes may affect the electrical characteristics experienced by the lead and/or the electrodes.

State-of-the-art assessment of lead condition may include measuring an impedance between a plurality of electrodes. A rise in the lead impedance may provide an indication that the lead condition has changed. This may be caused by various factors, such as deterioration of the lead, deterioration of the electrode, deterioration of connections between the electrode and the implantable device, and/or the physiological changes in the human body. Based upon the impedance measurements, state-of-the-art technology calls for assessing or concluding that there may be lead problems. However, a simple rise in lead impedance may not necessarily reflect actual lead problems. For example, physiological impedance changes may provide a false negative indication that there are lead problems. Additionally, the lack of a rise in lead impedance may provide a false positive indication that there are no problems with the leads or electrodes. For example, a lead problem may be masked by an apparent lack of change in lead impedance. This apparent lack of change in the lead impedance may actually be an increase in lead impedance (e.g., due to lead/electrode damage) being masked by a reduction in the physiologic impedance. The reduction in the physiologic impedance may counter-balance the rise in the electrode or lead impedance that may have been the result of actual damage. However, the result causes a false assessment of the actual condition of the lead and/or electrode. This could lead to improper delivery of therapeutic stimulation or improper assessment of monitored signals by the implantable device.

Other problems with the state-of-the-art include the fact that the insertion or placement of the lead and electrodes into the patient's body may be implemented incorrectly. For example, the insertion of the leads may be reversed compared to the originally intended position of the electrodes and/or leads. For example, the lead/electrode in a set that was originally intended to be positioned proximal to the implantable device may be inadvertently positioned in a distal position, while the intended distal electrode may inadvertently become the proximal electrode. Therapy stimulation being provided may be ineffectively administered or monitored signals may be errantly assessed due to the various errors described herein.

The present invention is directed to overcoming, or at least reducing, the effects of one or more of the problems set forth above.

SUMMARY OF THE INVENTION

In one aspect, the present invention comprises a method for determining a condition of a lead assembly coupled to an implantable medical device (IMD). A first impedance is determined relative to a first electrode and a reference electrode. The reference electrode may comprise a portion of the IMD. A second impedance is determined relative to a second electrode and the reference electrode. The first impedance is compared to the second impedance to determine an impedance difference. A determination is made whether the impedance difference is outside a predetermined tolerance range. An indication of a lead condition error is provided in response to determining that the impedance difference is outside the predetermined tolerance range. In another aspect, the present invention comprises a method for determining a condition of a lead assembly associated with an implantable medical device (IMD). The method comprises determining a first impedance relative to a first electrode and a reference electrode. A second impedance is determined relative to a second electrode and the reference electrode. A third impedance is determined relative to the first electrode and the second electrode. The method further comprises comparing the first impedance to the second impedance to determine an impedance difference. A determination is made whether the impedance difference is outside a predetermined tolerance range. The method additionally comprises providing an indication of a lead condition error in response to determining that the impedance difference is outside a predetermined tolerance range, and comparing the impedance difference to the third impedance. Based on the comparison of the impedance difference to the third impedance, a source of the lead condition error is identified. The source may include the first electrode, the second electrode, or a physiological impedance.

In another aspect, the present invention comprises a method for determining a condition of a lead assembly associated with an implantable medical device (IMD). The method comprises providing a first test signal to a first electrode coupled to the IMD through a first lead, and measuring a first signal artifact relating to a second electrode coupled to the IMD through a second lead. The first signal artifact results from the first test signal being applied to the first electrode. A second test signal is provided to the second electrode, and a second signal artifact relating to the first electrode is measured. The second signal artifact results from the second test signal being applied to the second electrode. The method further involves comparing the first signal artifact to the second signal artifact to determine a signal artifact differential. A determination is made as to whether the signal artifact differential is outside a predetermined tolerance range. Finally, the method includes providing an indication of a lead condition error in response to determining that the signal artifact differential is outside the predetermined tolerance range.

In yet another aspect, the present invention comprises a method for determining an orientation of a lead assembly associated with an implantable medical device (IMD). The method involves determining a first impedance relative to a first electrode and a reference electrode, as well as a second impedance relative to a second electrode and the reference electrode. The first impedance is compared to the second impedance to determine whether the first impedance is greater than the second impedance. Based on the comparison of the first and second impedances, the method comprises determining which of the first electrode and the second electrode is positioned distal to the reference electrode. In another aspect, the present invention comprises a method for determining the orientation of a lead assembly associated with an implantable medical device (IMD). A first test signal is provided to a first electrode coupled to the IMD through a first lead, and a first signal artifact relating to a second electrode coupled to the IMD through a second lead is measured. The first signal artifact results from the first test signal being applied to the first electrode. A second test signal is provided to the second electrode, and a second signal artifact relating to the first electrode is measured. The second signal artifact results from the second test signal being applied to the second electrode. The first signal artifact is compared to the second signal artifact to determine whether the first signal artifact is greater than the second signal artifact. A determination is made as to which of the first electrode and the second electrode is distal to the IMD in response to comparing the first and second signal artifacts.

In another aspect, the present invention comprises a system for performing a lead condition assessment and/or a lead orientation determination associated with an implantable medical device (IMD). The system includes an implantable medical device (IMD) for delivering an electrical signal to a patient's body; a first electrode coupled to the IMD and to a first portion of a patient's body; a second electrode coupled to coupled the IMD and to a second portion of a patient's body; and an external device to communicate with the IMD. The system comprises a controller to determine a first impedance relative to a first electrode and a reference electrode. The controller is also adapted to determine a second impedance relative to a second electrode and the reference electrode. The controller is also adapted to compare the first impedance and the second impedance to determine an impedance difference, and to determine whether the impedance difference is outside a predetermined tolerance range. The system is also adapted to provide an indication of a lead condition error in response to determining that the impedance difference is outside the predetermined tolerance range. In another aspect, the present invention comprises a system for performing a lead condition assessment and/or a lead orientation determination associated with an implantable medical device (IMD). The system includes an implantable medical device (IMD) for delivering an electrical signal to a patient's body; a first electrode coupled to the IMD and to a first portion of the patient's body; a second electrode coupled to the IMD and to a second portion of the patient's body; and an external device to communicate with the IMD. The IMD includes a stimulation unit to providing a first test signal to a first electrode coupled to the IMD through a first lead and to provide a second test signal to a second electrode coupled to the IMD through a second lead. The IMD also includes a signal unit to measure a first signal artifact relating to a second electrode coupled to the IMD through a second lead. The first signal artifact results from the first test signal being applied to the first electrode. The signal unit is also adapted to measure a second signal artifact relating to the first electrode, which results from the second test signal being applied to the second electrode. The IMD also includes a controller to compare the first signal artifact to the second signal artifact to determine whether the first signal artifact is greater than the second signal artifact and in response, to determine which of the first and the second electrodes is distal to the IMD. The IMD also includes a communication unit to communicate data relating to a lead orientation of the first and second leads to the external device based upon the determination the first electrode is in at least one of a distal and a proximal position.

In yet another aspect of the present invention, a computer readable program storage device encoded with instructions is provided for performing a method for determining a condition of a lead assembly associated with an implantable medical device (IMD). The computer, performs a method which comprises: determining a first impedance relative to a first electrode and a reference electrode; determining a second impedance relative to a second electrode and the reference electrode; comparing the first impedance to the second impedance to determine an impedance difference; determining whether the impedance difference is outside a predetermined tolerance range; and providing an indication of a lead condition error in response to determining that the impedance difference is outside the predetermined tolerance range. In yet another aspect of the present invention, a computer readable program storage device encoded with instructions is provided for performing a lead condition assessment and/or a lead orientation determination associated with an implantable medical device (IMD). The computer performs a method, which comprises: providing a first test signal to a first electrode coupled to the IMD through a first lead; measuring a first signal artifact relating to a second electrode coupled to the IMD through a second lead, the first signal artifact resulting from the first test signal being applied to the first electrode; providing a second test signal to the second electrode; measuring a second signal artifact relating to the first electrode, the second signal artifact resulting from the second test signal being applied to the second electrode; comparing the first signal artifact to the second signal artifact to determine whether the first signal artifact is greater than the second signal artifact; determining which of the first electrode and the second electrode is distal to the IMD in response to determining whether the first signal artifact is greater than the second signal artifact.

BRIEF DESCRIPTION OF THE DRAWINGS

The invention may be understood by reference to the following description taken in conjunction with the accompanying drawings, in which like reference numerals identify like elements, and in which:

FIG. 4 provides a more detailed block diagram depiction of the signal detection unit of FIG. 3, in accordance with one illustrative embodiment of the present invention;

FIG. 5 provides a block diagram depiction of an impedance unit of FIG. 3, in accordance with one illustrative embodiment of the present invention;

Figure 1A:
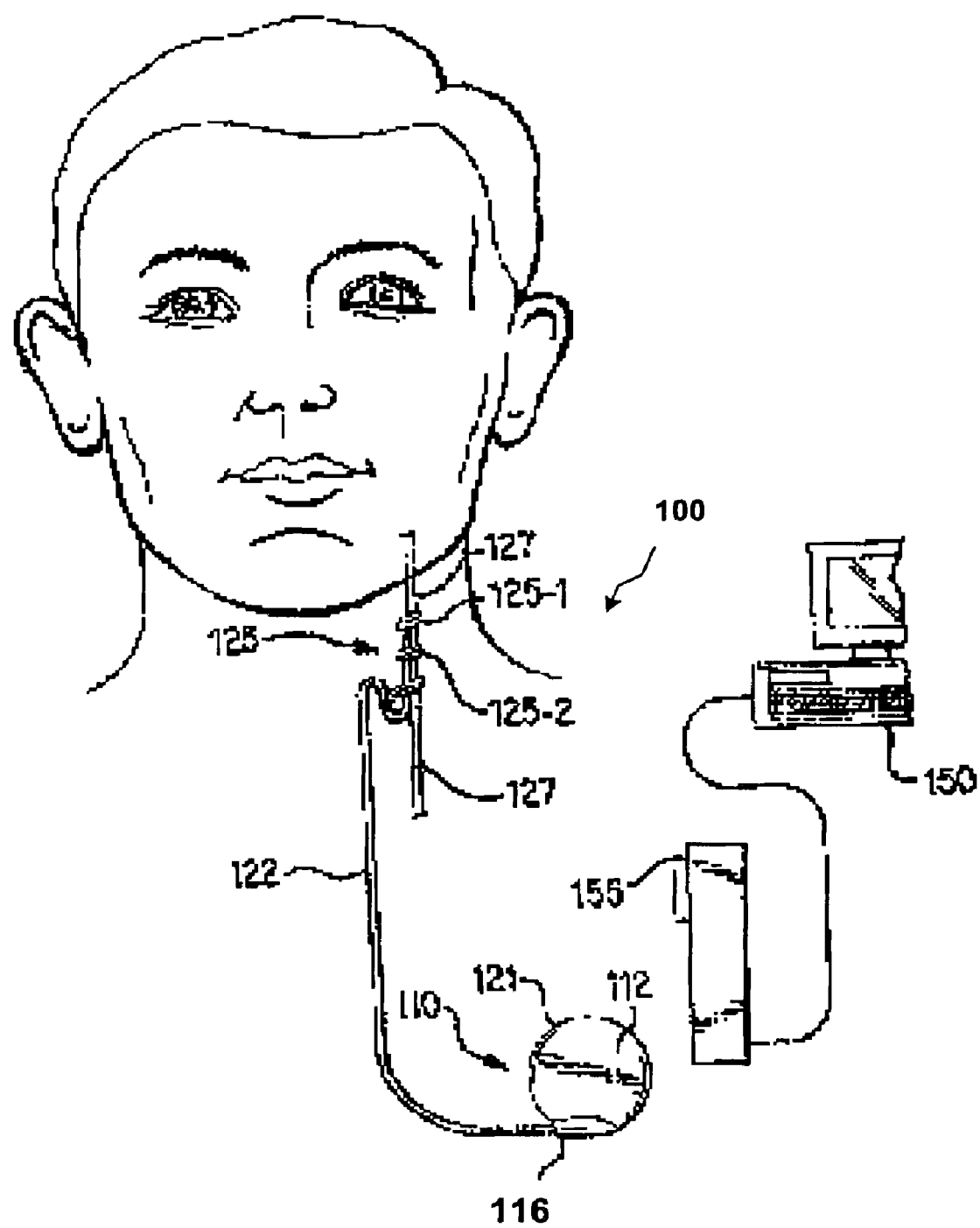
FIGS. 1A-1D provide stylized diagrams of an implantable medical device implanted into a patient's body for providing stimulation to a portion of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

FIGS. 1A-1D depict a stylized implantable medical system 100 for implementing one or more embodiments of the present invention. FIGS. 1A-1D illustrate a signal generator 110 having a main body 112 comprising a case, or shell 121, with an electrical connector 116 in a header 114 (FIG. 1C) for connecting to lead assembly 122. The signal generator 110 is implanted in the patient's chest in a pocket or cavity formed by the implanting surgeon just below the skin (indicated by a dotted line 145, FIG. 1B), similar to the implantation procedure for a pacemaker pulse generator.

A stimulating electrode assembly 125, preferably comprising an electrode pair, is conductively connected to the distal end of the insulated electrically conductive lead assembly 122, which preferably comprises a pair of lead wires (one wire for each electrode of an electrode pair). Lead assembly 122 is coupled at its proximal end to the electrical connector 116 on header 114. The electrode assembly 125 is surgically coupled to the patient's tissue, e.g., a vagus nerve 127 in the patient's neck. The present invention is suitable for use in implantable medical devices connected to any body tissue, e.g., a pacemaker coupled to heart tissue. The electrode assembly 125 preferably comprises a bipolar stimulating electrode pair (FIG. 1D), such as the electrode pair described in U.S. Pat. No. 4,573,481 issued Mar. 4, 1986 to Bullara.

As used herein, the term lead assembly refers to the combination of the lead individually and the electrodes coupled thereto. Persons of skill in the art will appreciate that many electrode designs could be used in the present invention. For embodiments of the present invention involving vagus nerve stimulation, two electrodes are preferably wrapped about the vagus nerve, and the electrode assembly 125 is preferably secured to the nerve 127 by a spiral anchoring tether 128 (FIG. 1D) such as that disclosed in U.S. Pat. No. 4,979,511 issued Dec. 25, 1990 to Reese S. Terry, Jr., and assigned to the same assignee as the instant application. Lead assembly 122 is secured, while retaining the ability to flex with movement of the chest and neck, by a suture connection 130 to nearby tissue.

In one embodiment of the present invention involving nerve stimulation, the open helical design of the electrode assembly 125 (described in detail in the above-cited Bullara patent), which is self-sizing and flexible, minimizes mechanical trauma to the nerve and allows body fluid interchange with the nerve. The electrode assembly 125 preferably conforms to the shape of the nerve, providing a low stimulation threshold by allowing a large stimulation contact area with the nerve. Structurally, the electrode assembly 125 comprises two electrode ribbons (not shown) of a conductive material such as platinum, iridium, platinum-iridium alloys, and/or oxides of the foregoing. The electrode ribbons are individually bonded to an inside surface of an elastomeric body portion of the two spiral electrodes 125-1 and 125-2 (FIG. 1D), which may comprise two spiral loops of a three-loop helical assembly. The elastomeric body portion of each loop preferably comprises silicone rubber, and the third loop 128 (which typically has no electrode) acts as the anchoring tether 128 for the electrode assembly 125.

The lead assembly 122 may comprise two distinct lead wires or a coaxial cable whose two conductive elements are respectively coupled to one of the conductive electrode ribbons 125-1 and 125-2. One suitable method of coupling the lead wires or cable to the electrodes comprises a spacer assembly such as that disclosed in U.S. Pat. No. 5,531,778, although other known coupling techniques may be used.

Figure 1B:
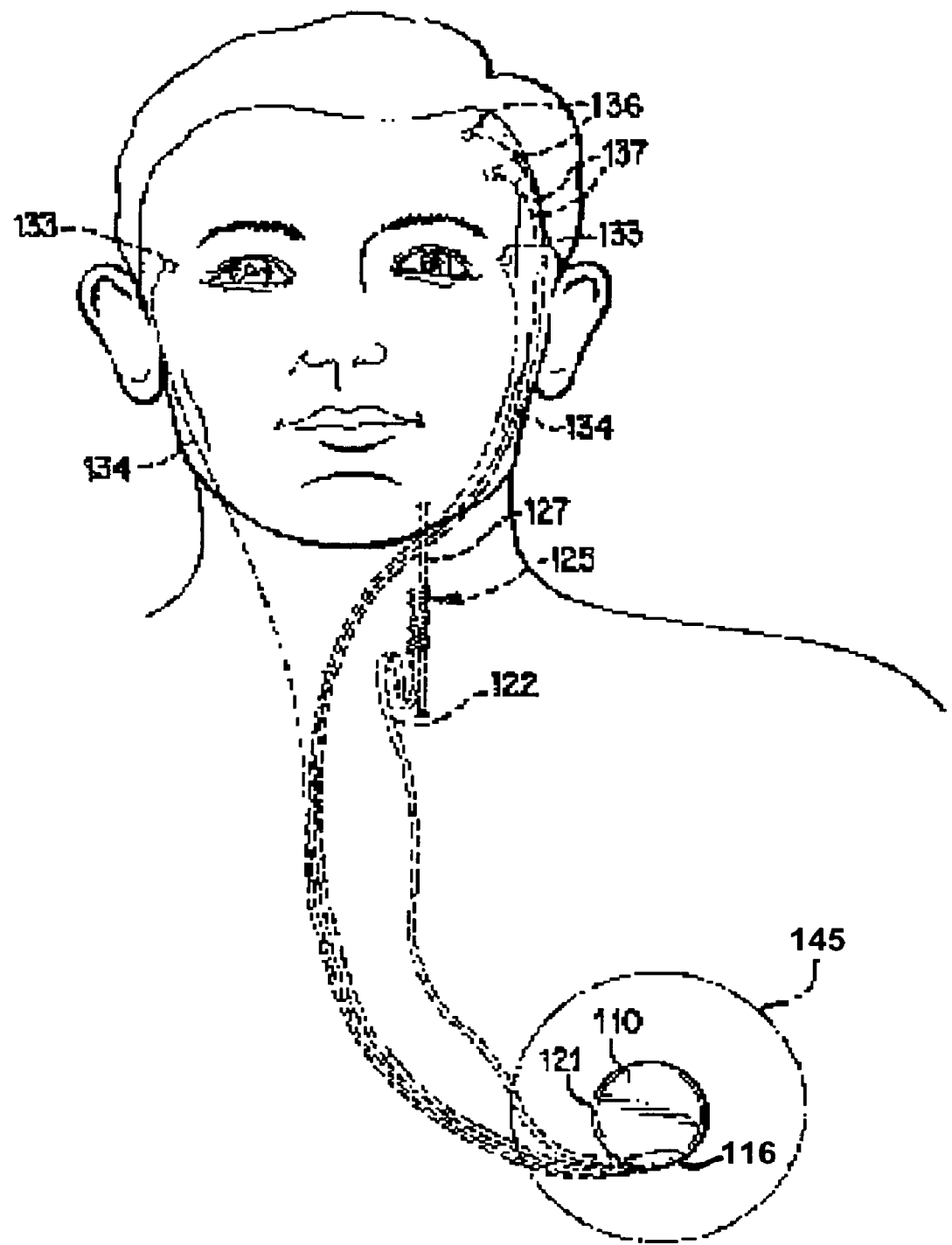
Figure 1C:
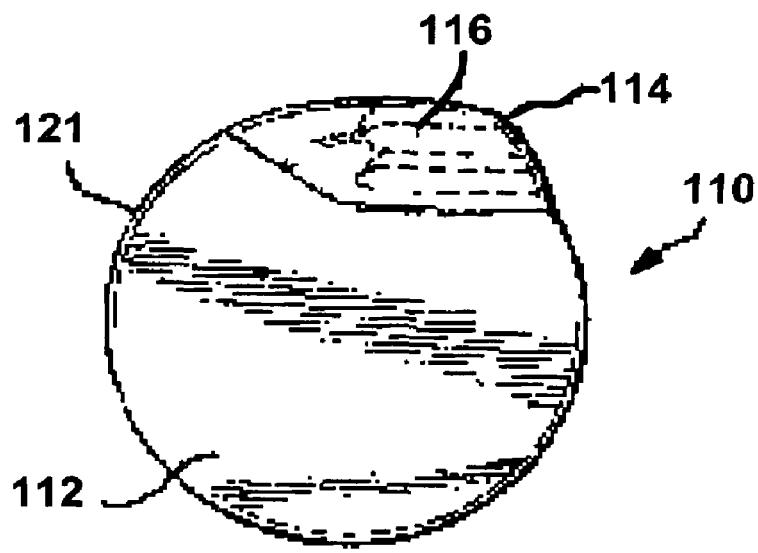

In certain embodiments of the present invention, sensing elements may be used to provide data to the implantable medical system 100 concerning one or more body parameters. Although exemplary sensors are disclosed herein, persons of skill in the art will appreciate that the present invention is not limited to particular embodiments. Referring to FIG. 1B, eye movement sensing electrodes 133 may be implanted at or near an outer periphery of each eye socket in a suitable location to sense muscle movement or actual eye movement. The electrodes 133 may be electrically connected to leads 134 implanted via a catheter or other suitable means (not shown) and extending along the jawline through the neck and chest tissue to the signal generator 110. When included in systems of the present invention, the sensing electrodes 133 may be utilized for detecting rapid eye movement (REM) in a pattern indicative of a disorder to be treated, as described in greater detail below. Alternatively or additionally, the electrodes in lead assembly 122 may be used as sensing electrodes.

Alternatively or additionally, EEG sensing electrodes 136 may optionally be implanted in spaced apart relation through the skull, and connected to leads 137 implanted and extending along the scalp and temple and then to the signal generator 110 in the same manner as described above for the eye movement electrode leads. Electrodes 133 and 136, or other types of sensors may be used in some embodiments of the invention to trigger administration of the electrical stimulation therapy to the vagus nerve 127 via electrode assembly 125. Use of such sensed body signals to trigger or initiate stimulation therapy is hereinafter referred to as a "feedback" or "active" stimulation. Other embodiments of the present invention utilize a stimulation therapy delivered according to a programmed on/off duty cycle without the use of sensors to trigger therapy delivery. This type of delivery may be referred to as "passive," "non-feedback," or prophylactic stimulation. Both active and passive stimulation may be combined or delivered by a single IMD 200 according to the present invention. Either or both modes may be appropriate to treat the particular disorder diagnosed in the case of a specific patient under observation. The therapeutic electrical signal may be a continuous or pulsed signal; either type of signal may be applied periodically or intermittently to the vagus nerve.

The signal generator 110 may be programmed with an external computer 150 (FIG. 1A) using programming software of the type copyrighted by the assignee of the instant application with the Register of Copyrights, Library of Congress, or other suitable software based on the description herein, and a programming wand 155 may be used to facilitate radio frequency (RF) communication between the computer 150 and the signal generator 110. The wand 155 and software permit noninvasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator.

A wide variety of stimulation therapies may be provided in implantable medical systems 100 of the present invention. Different types of nerve fibers (e.g., A, B, and C fibers being different fibers targeted for stimulation) respond differently to stimulation from electrical signals. More specifically, the different types of nerve fibers have different conduction velocities and stimulation thresholds and, therefore, differ in their responsiveness to stimulation. Certain pulses of an electrical stimulation signal, for example, may be below the stimulation threshold for a particular fiber and, therefore, may generate no action potential in the fiber. Thus, smaller or narrower pulses may be used to avoid stimulation of certain nerve fibers (such as C fibers) and target other nerve fibers (such as A and/or B fibers, which generally have lower stimulation thresholds and higher conduction velocities than C fibers). Additionally, techniques such as pre-polarization may be employed wherein particular nerve regions may be polarized before a more robust stimulation is delivered, which may better accommodate particular electrode materials. Furthermore, opposing polarity phases separated by a zero current phase may be used to excite particular axons or postpone nerve fatigue during long-term stimulation.

Embodiments of the present invention provide for assessing a lead and/or an electrode condition associated with an implantable medical device system, which includes an implantable medical device, a plurality of leads and a plurality of electrodes. Various electrodes and corresponding leads may be implanted into a portion of a patient's body, such as a portion of a vagus nerve. The implantable medical device may be coupled operatively to the electrodes via corresponding leads. Changing conditions in the human body, to the leads, and/or to the electrodes, may cause a change in the operation of the implantable medical device. These changes may affect the treatment of a patient having the implantable medical device. Embodiments of the present invention provide for monitoring the condition of the leads, electrodes, and/or the surrounding portions of the human body to assess the condition of the leads and/or the electrodes. Various impedance calculations and signal measurements associated with the various leads and/or electrodes may be performed and analyzed to determine the lead conditions.

Additionally, embodiments of the present invention may be used to provide a lead orientation detection. Various leads and electrodes may be implanted in a predetermined orientation. A particular electrode may be implanted as a distal electrode relative to the implantable medical device or other reference electrode, wherein another electrode may be implanted as a proximal electrode in relation to the implantable medical device or other reference electrode. Embodiments of the present invention may be used to perform an automated check of the lead orientation and compare it with a predetermined, desired lead orientation. Upon an indication or detection that the implanted lead orientation varies from the predetermined lead orientation, the implantable medical device may provide a warning or a message. Based upon the message/warning relating to the lead orientation and/or the lead conditions provided by embodiments of the present invention, one or more corrective actions may be performed by an external entity, such as a physician.

Figure 2:
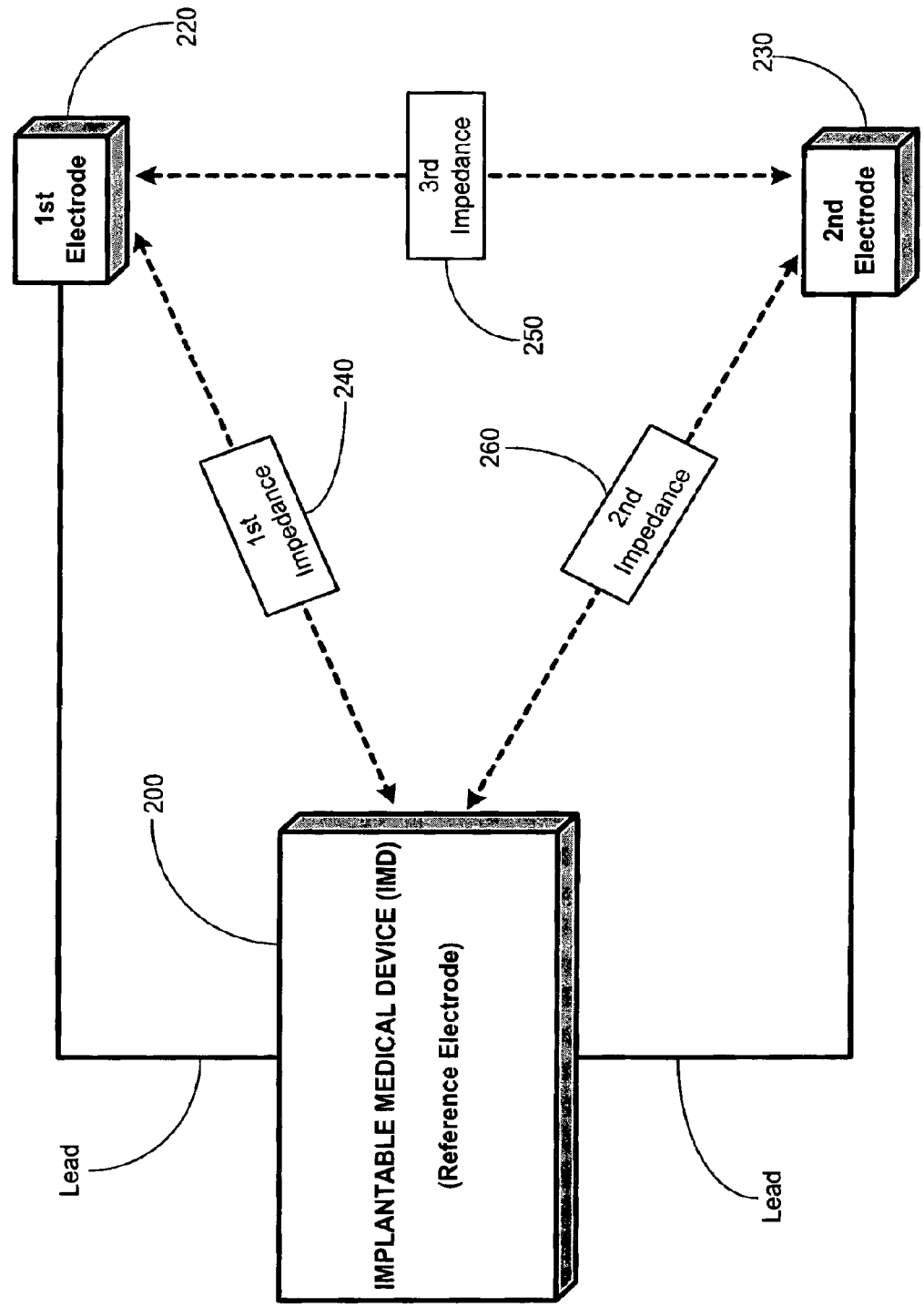
FIG. 2 provides a layout depiction of an implantable medical device and associated lead and electrodes, in accordance with one illustrative embodiment of the present invention.

Turning now to FIG. 2, a block diagram depiction of an implantable medical device 200, coupled to a first electrode 220 and a second electrode 230, is illustrated. The implantable medical device 200 (IMD) is capable of delivering a stimulation signal to a portion of the patient's body (e.g., a portion of a vagus nerve). The electrodes may be affixed to a portion of the patient's body, wherein the IMD 200 provides the stimulation signal to the electrodes 220, 230. Alternatively, a reference electrode independent from IMD 200 may be used instead of the IMD 200.

The first and second electrodes 220, 230, are coupled to the IMD 200 via corresponding leads. In one embodiment, the first electrode 220 may be positioned/implanted in a proximal orientation relative to the IMD 200. The second electrode 230 may be positioned in a distal orientation relative to the IMD 200. Embodiments of the present invention provide for measuring various impedances in relation to the IMD and the electrodes 220, 230. The IMD 200 may measure a first impedance 240, which is an impedance of the first electrode relative to a reference electrode that, in one embodiment, comprises the case 121 of the IMD 200. The first impedance may be indicative of the lead impedance of the lead that couples the first electrode 220 to the IMD 200. The IMD 200 may also measure a second impedance 260, which is the impedance of the second electrode 230 in relation to a reference electrode, e.g., the case 121 of the IMD 200. This impedance may provide the lead impedance of the lead that couples the second electrode 230 to the IMD 200. Further, the IMD 200 may measure the third impedance 250, which may be the impedance of the first electrode 220 relative to the second electrode 230.

The various impedances described herein may be used to assess the lead orientation relative to an expected lead orientation and/or an assessment of various lead/electrode conditions. In one embodiment, the first impedance 240 and the second impedance 260 may be analyzed and compared such that an impedance difference between the first and second impedances 240, 260, may be indicative of a particular lead condition. For example, if the difference between the first impedance and the second impedance exceeds a pre-determined threshold range or tolerance range, a faulty lead condition may be deemed to have taken place. The differences between the first impedance and the second impedance 240, 260, may then also be analyzed in conjunction with the third impedance 250 for further analysis of the lead condition. Additionally, the impedances described in FIG. 2 may also be used to determine whether the lead orientation of the leads described in FIG. 2 complies with expected lead orientation. Further details relating to the impedance measurements are provided below.

In one embodiment, the lead impedances 240, 260, may be measured by employing a test signal that may be sent to the first and/or the second electrodes via corresponding leads. The test signal may be of a variety of types of signals, such as a current pulse signal. In one embodiment, the test signal may be a pulse signal of approximately 0.25 milliamps in amplitude with a pulse width of 130 microseconds. The resultant voltage associated with the electrode under test may be measured. The current and the voltage values may then be used to calculate the impedance. Additionally, when one electrode is exposed to a test pulse, a resultant artifact signal appearing on another electrode may be measured in order to perform the lead orientation and/or the lead condition assessments described herein. Additionally, the signal artifact may be analyzed to further evaluate a resistive characteristic and/or a capacitive characteristic.

Figure 1D:
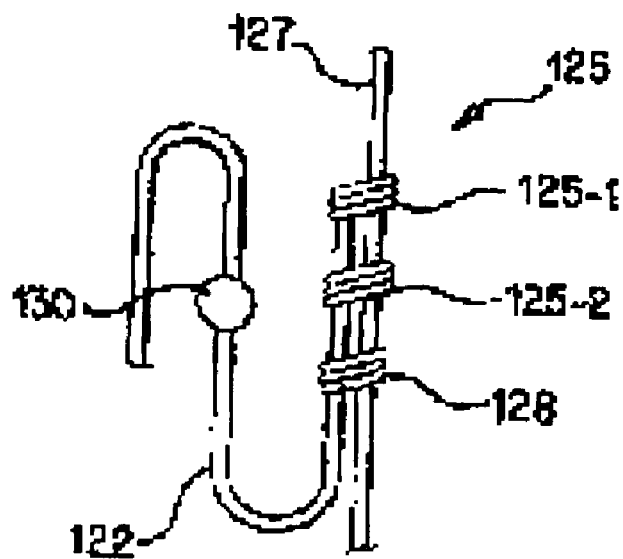
Figure 3:
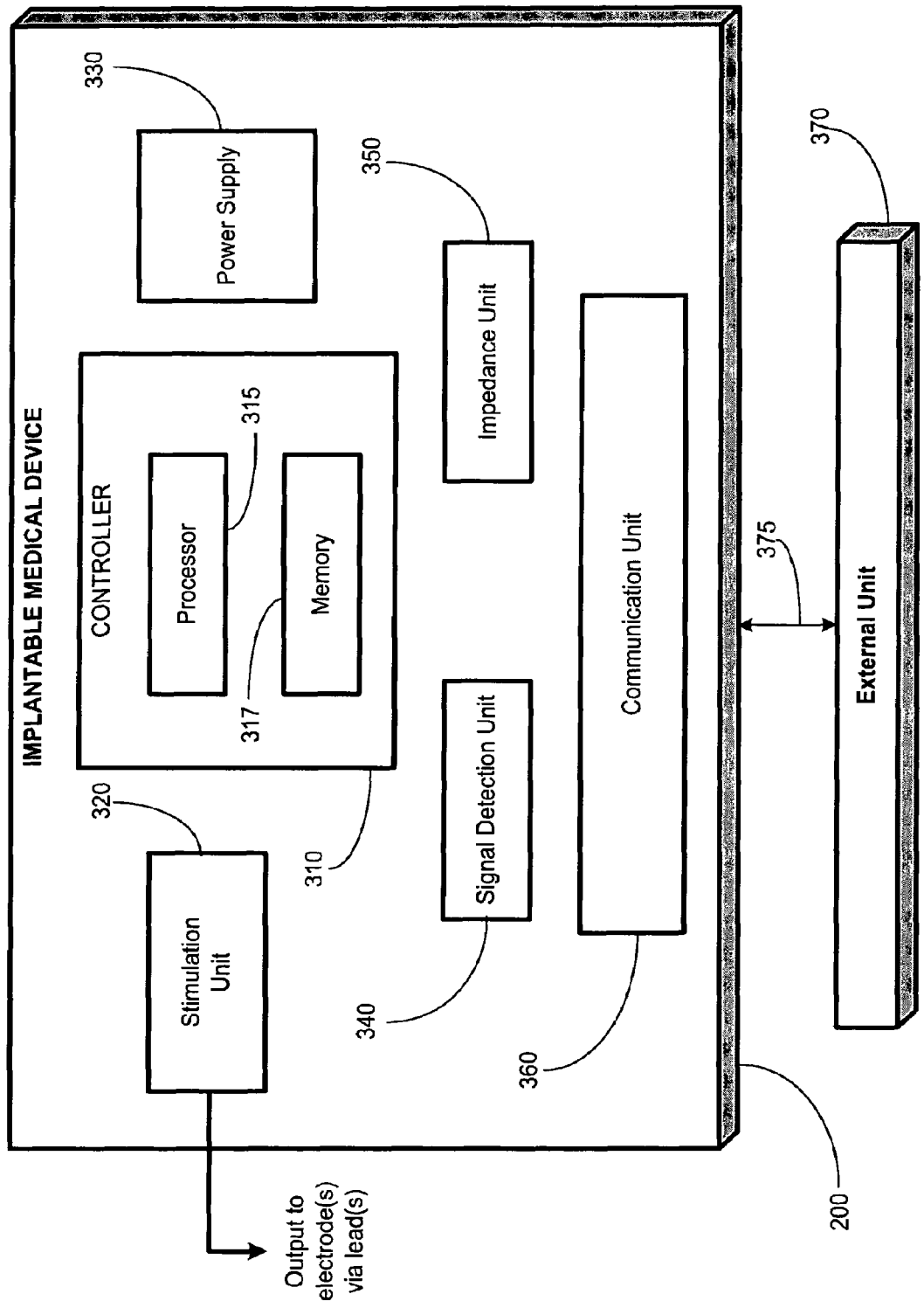
FIG. 3 provides a block diagram depiction of an implantable medical device, in accordance with one illustrative embodiment of the present invention.

Turning now to FIG. 3, a block diagram depiction of the IMD 200, in accordance with one illustrative embodiment of the present invention is illustrated. The IMD 200 may be used for stimulation to treat various disorders, such as epilepsy, depression, bulimia, heart rhythm disorders, etc. The IMD 200 may be coupled to various leads, e.g., 122, 134, 137 (FIGS. 1A, 1B, 1D). Stimulation signals used for therapy may be transmitted from the IMD 200 to target areas of the patient's body, specifically to various electrodes associated with the leads 122. Stimulation signals from the IMD 200 may be transmitted via the leads 122 to stimulation electrodes associated with the electrode assembly 125 (FIG. 1A). Further, signals from sensor electrodes, e.g., 133, 13.6 (FIG. 1B) associated with corresponding leads, e.g., 134, 137, may also traverse the leads back to the IMD 200.

The implantable medical device 200 may comprise a controller 310 capable of controlling various aspects of the operation of the IMD 200. The controller 310 is capable of receiving internal data and/or external data and generating and delivering a stimulation signal to target tissues of the patient's body. For example, the controller 310 may receive manual instructions from an operator externally, or may perform stimulation based on internal calculations and programming. The controller 310 is capable of affecting substantially all functions of the IMD 200.

The controller 310 may comprise various components, such as a processor 315, a memory 317, etc. The processor 315 may comprise one or more micro controllers, microprocessors, etc., that are capable of performing various executions of software components. The memory 317 may comprise various memory portions where a number of types of data (e.g., internal data, external data instructions, software codes, status data, diagnostic data, etc.) may be stored. The memory 317 may comprise random access memory (RAM) dynamic random access memory (DRAM), electrically erasable programmable read-only memory (EEPROM), flash memory, etc.

The IMD 200 may also comprise a stimulation unit 320. The stimulation unit 320 is capable of generating and delivering stimulation signals to one or more electrodes via leads. A number of leads 122, 134, 137 may be coupled to the IMD 200. Therapy may be delivered to the leads 122 by the stimulation unit 320 based upon instructions from the controller 310. The stimulation unit 320 may comprise various circuitry, such as stimulation signal generators, impedance control circuitry to control the impedance "seen" by the leads, and other circuitry that receives instructions relating to the type of stimulation to be performed. The stimulation unit 320 is capable of delivering a controlled current stimulation signal over the leads 122.

The IMD 200 may also comprise a power supply 330. The power supply 330 may comprise a battery, voltage regulators, capacitors, etc., to provide power for the operation of the IMD 200, including delivering the stimulation signal. The power supply 330 comprises a power-source battery that in some embodiments may be rechargeable. In other embodiments, a non-rechargeable battery may be used. The power supply 330 provides power for the operation of the IMD 200, including electronic operations and the stimulation function. The power supply 330 may comprise a lithium/thionyl chloride cell or a lithium/carbon monofluoride cell. Other battery types known in the art of implantable medical devices may also be used.

The IMD 200 also comprises a communication unit 360 capable of facilitating communications between the IMD 200 and various devices. In particular, the communication unit 360 is capable of providing transmission and reception of electronic signals to and from an external unit 370. The external unit 370 may be a device that is capable of programming various modules and stimulation parameters of the IMD 200. In one embodiment, the external unit 370 is a computer system that is capable of executing a data-acquisition program. The external unit 370 may be controlled by a healthcare provider, such as a physician, at a base station in, for example, a doctor's office. The external unit 370 may be a computer, preferably a handheld computer or PDA, but may alternatively comprise any other device that is capable of electronic communications and programming. The external unit 370 may download various parameters and program software into the IMD 200 for programming the operation of the implantable device. The external unit 370 may also receive and upload various status conditions and other data from the IMD 200. The communication unit 360 may be hardware, software, firmware, and/or any combination thereof. Communications between the external unit 370 and the communication unit 360 may occur via a wireless or other type of communication, illustrated generally by line 375 in FIG. 3.

The IMD 200 may also comprise a signal detection unit 340. The signal detection unit 340 is capable of receiving the signals relating to the first and second electrodes and their corresponding leads. Voltage signals and/or resultant artifact signals from the first and second electrodes 220, 230 (FIG. 2) may be received by the signal detection unit 340. The signal detection unit 340 is capable of performing various filtering and/or amplification to condition the detected signals. The signal detection unit 340 detects various characteristics that may lead to the measurement of an impedance. A more detailed illustration of the signal detection unit is provided in FIG. 4 and accompanying description below.

The IMD 200 may also comprise an impedance unit 350. The impedance unit 350 is capable of performing various comparisons of the voltages and/or other signals relating to the leads as well as to the first and second electrodes 220, 230. The impedance unit 350 is capable of calculating the impedance based upon various comparisons to determine the impedance of a lead/electrode. A more detailed illustration and description of the impedance unit 350 is provided in FIG. 5 and accompanying description below. Additionally or alternatively, information necessary to perform these calculations may be provided via communication unit 360 to external unit 370 for computation.

Turning now to FIG. 4, a block diagram depiction of the signal detection unit 340 in accordance with an illustrative embodiment of the present invention is provided. The signal detection unit 340 may comprise a filter unit 410 and an amplifier unit 420. The filter unit 410 may comprise various signal filters, such as band-pass filters, high-pass filters, low-pass filters, etc. These filters may filter voltage signals, current signals, etc., received by the IMD 200. The filtered signals may be amplified and/or buffered by the amplifier unit 420. One or more amplifiers in the amplifier unit 420 may amplify the signals received from the first electrode 220 and/or the second electrode 230.

Turning now to FIG. 5, a block diagram depiction of the impedance unit 250 in accordance with an illustrative embodiment of the present invention is provided. The impedance unit 350 may comprise a comparator unit 530 and an impedance calculation unit 540. The comparator unit 530 may comprise various comparators that are capable of comparing numerous electrical indications of the signal present on the first electrode and/or the second electrode 220-230. For example, indications of the first impedance, such as the voltage relative to the first electrode to a reference electrode, may be compared to the voltage relative to the second electrode 230 to a reference electrode. Based upon these comparisons, an impedance comparison may be based using Ohms Law. In an alternative embodiment, the comparator unit 530 may compare impedance calculations, where the first impedance 240 may be compared to the second impedance 260 and/or to the third impedance 250. Alternatively, the comparator unit 530 may compare resultant artifact signals from the first and second electrodes 220, 230. Alternatively, measurements of these electrical indications may be recorded for subsequent computational comparison by processor 315 or external unit 370.

The impedance calculation unit 540 may comprise various circuitry to calculate the first impedance 240, the second impedance 260 and/or the third impedance 250. The impedance may be calculated using various techniques (e.g., the known current level of the test pulse delivered to an electrode being divided by the resultant voltage) to calculate the impedance. The impedance calculation unit 540 is capable of calculating various impedances of leads/electrodes associated with the IMD 200. The IMD 200 may then use the various impedance calculations to make assessments relating to the lead conditions and/or lead orientation. Alternatively, measurements of voltages and/or currents may be recorded for subsequent computational determination and/or comparison of impedance by processor 315 or external unit 370.

Figure 6:
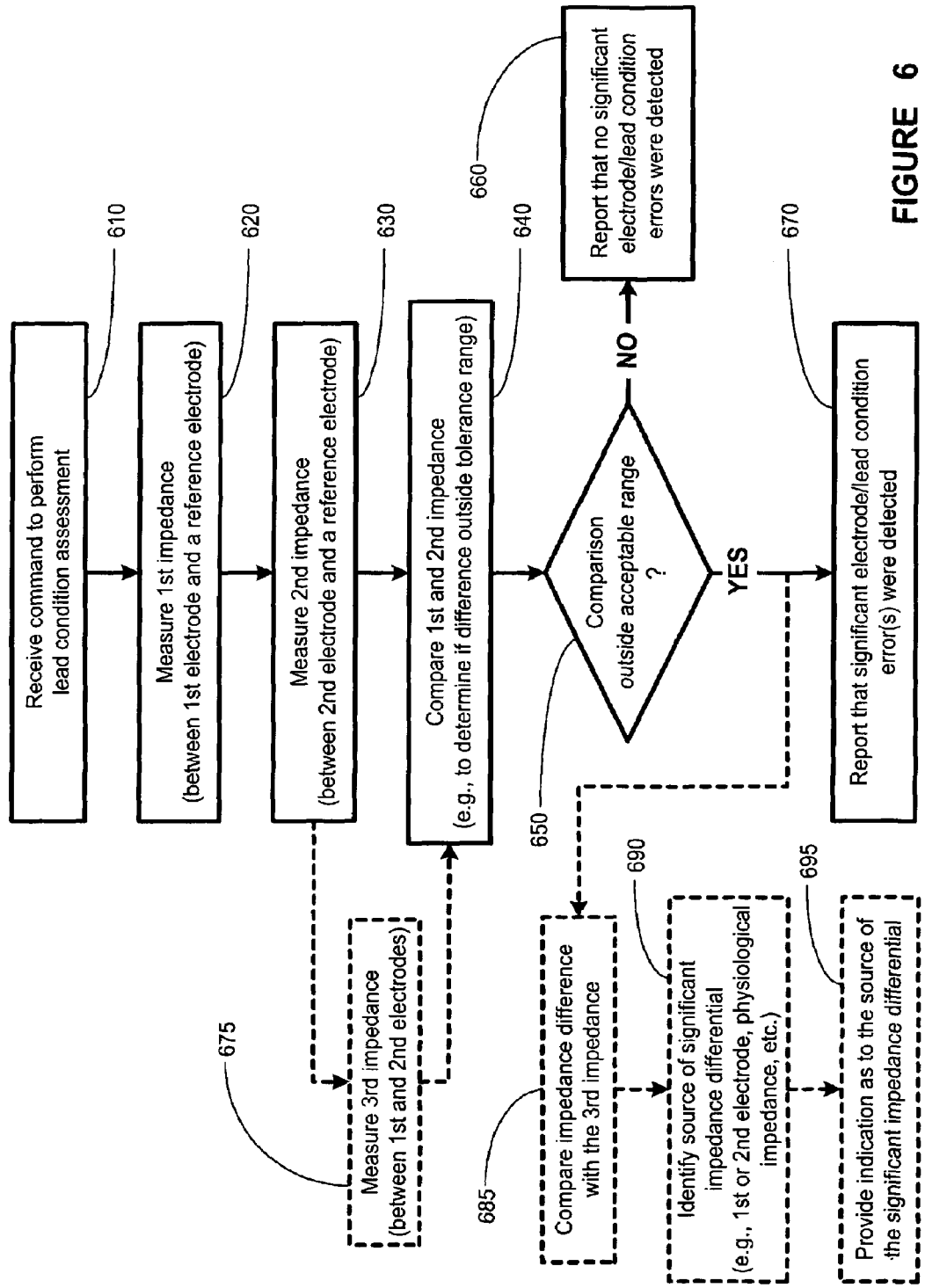
FIG. 6 provides a flowchart depiction of a method of performing a lead condition assessment, in accordance with one illustrative embodiment of the present invention.

Turning now to FIG. 6, a flowchart depiction of one embodiment of performing a lead condition assessment, in accordance with an embodiment of the present invention, is illustrated. The IMD 200 may receive a command to perform a lead condition assessment (block 610). The command to perform the lead condition assessment may come from an external source via the communication unit 360. In an alternative embodiment, the IMD 200 may be programmed to generate a signal to initiate the lead condition assessment. In yet another alternative embodiment, a predetermined condition may trigger the initiation of the lead condition assessment process. Upon initiation of the lead condition assessment test, the IMD 200 may measure the first impedance 240, which may be between the first electrode 220 and a reference electrode that in one embodiment comprises the case 121 of the IMD 200 (block 620). The measurement of the first impedance 240 may entail delivering a signal, such as a test pulse signal, to the first electrode. The IMD 200 measures the resultant voltage in response to the current test signal delivered to the electrode 220.

Upon detection of the voltage resulting from the delivered test current, the impedance may be calculated. The IMD 200 may also measure the second impedance 260, which may be the impedance between the second electrode 230 relative to a reference electrode (block 630). The second impedance 260 may be measured by providing a test current signal to the second electrode 230 and measuring the resultant voltage. The impedance of the second electrode 230 relative to the reference electrode may then be calculated. Upon measurements of the first and the second impedances, the IMD 200 may compare the first and second impedances (block 640). This comparison may be made to determine whether the differences between the first and second impedances are above a predetermined threshold (block 640). Alternatively or additionally, the comparison may be an evaluation of the ratio of impedances or the comparison of each individual impedance to preset limits.

Pre-determined and/or previously calculated indications of the expected values of the first and second impedances may be stored in the IMD 200. The fact that the second electrode may be substantially distal to the proximally positioned first electrode 220 may result in expected and/or pre-determined impedance differences between the first and the second impedances 240, 260. Taking into account the expected impedance differential, the comparison of the actual first and second measured impedances may indicate an impedance difference that is above or below an expected threshold or tolerance range. A determination is made whether the comparison of the first and second impedances is indeed beyond a threshold/tolerance range (block 650). Upon a determination that the difference between the first and second impedances are not substantially above or below the predetermined threshold or tolerance range, a report of no significant lead condition problems may be provided by the IMD 200 (block 660). This indication may be stored in the IMD 200 and/or communicated to an external entity, such as a physician, via the communication unit 360. Upon a determination that the comparison of the first and the second impedances are either below or above the predetermined range of tolerance or have excessive differences or ratios, an indication may be provided that the electrodes and/or the leads conditions are suspect (block 670).

The indication that the lead condition is suspect may be communicated to the external unit 370 via the communication unit 360. The substantial difference above or below the predetermined threshold range may be indicative of the fact that the electrode path relating to the first and/or the second electrodes 220-230 may contain a problem. A warning signal may be provided by the IMD 200 to warn a physician that further analysis and trouble-shooting may be required.

FIG. 6 also illustrates an alternative embodiment that may be employed by the IMD 200 in conjunction with the steps described above. The steps/paths associated with the alternative embodiment are denoted by dotted lines. Upon measuring the first and second impedances 240, 260, the IMD 200 may measure a third impedance 250, which may provide an indication of an impedance between the first and the second electrode (block 675). Upon measurements of the first, second, and third impedances 240-260, the IMD 200 may perform the comparison between the first and the second impedances to determine if the differences above are below a predetermined threshold.

Upon an indication that the difference between the first and the second impedances are outside the acceptable threshold/tolerance range (block 650), the IMD 200 may compare the first, second and third impedances (block 685). For example, the difference between the first and the second impedances may be compared to the third impedance 250 in order to determine a likely source of any significant impedance differences. For example, the assessment of comparison for differences between the first and the second impedances to the third impedance 250 may provide an indication whether the source of the impedance difference is the first electrode 220, or the second electrode 230, and/or another factor (e.g., a third factor). The third factor may include a physiologic change in the impedance. For example, scar tissue or other changes in the human body surrounding the first and the second electrodes may cause a change in the physiologic impedance, thereby hampering the delivery of stimulation. Therefore, based upon the comparisons of the various impedances, the IMD 200 may identify the likely source of the significant impedance differences (block 690). Upon identifying the source of the significant impedance differences, the IMD 200 may provide information relating to the significant source of impedance, along with the indication that the impedance differences between the first and the second impedances is above or below a predetermined threshold, as indicated by blocks 695 and 670. Therefore, the IMD 200 is capable of providing information relating to lead conditions and possible indications of the cause of the impedance changes and/or changes in the lead/electrode conditions. A physician may then take corrective action to modify the operation of the IMD 200.

Figure 7:
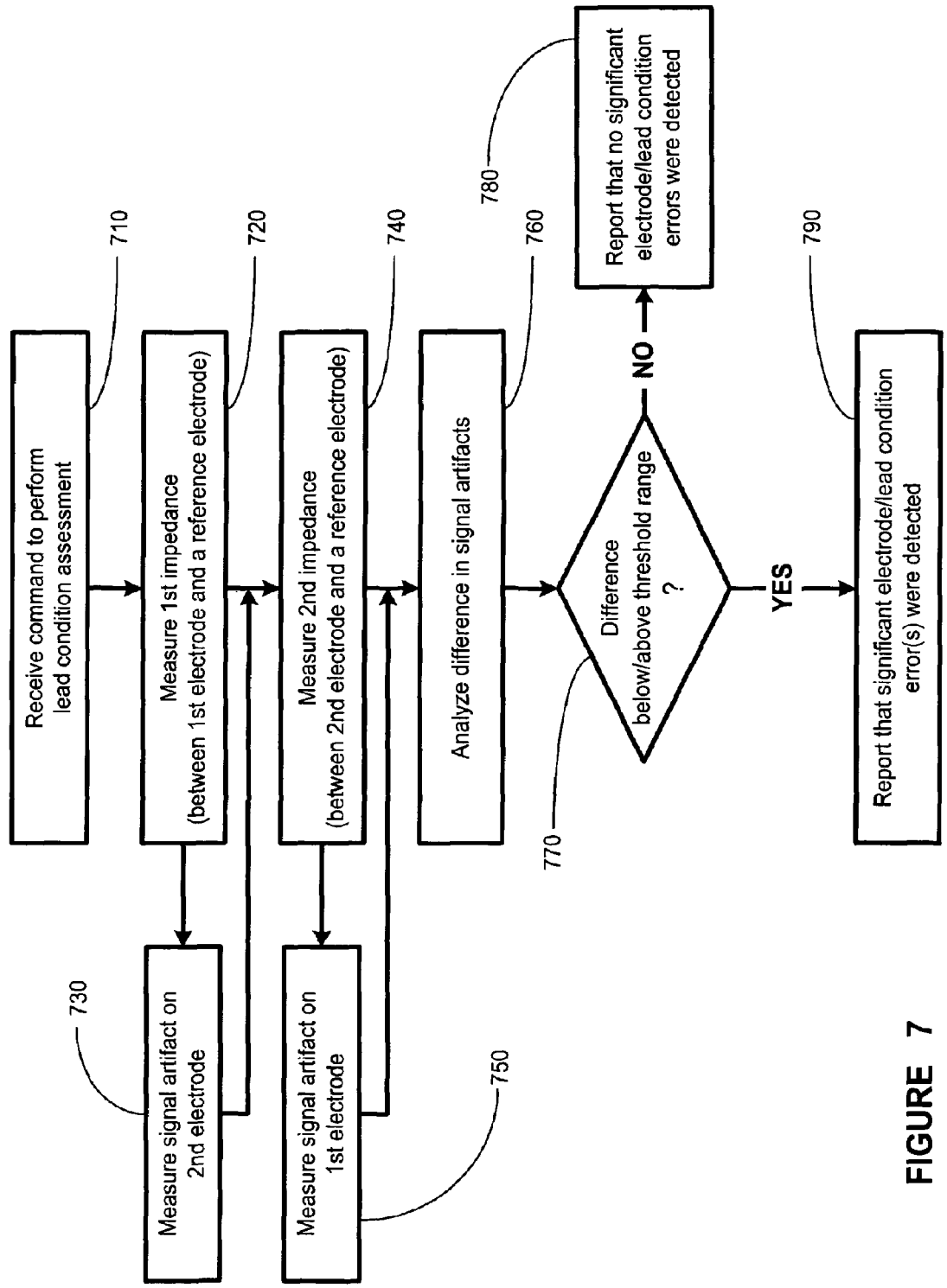
FIG. 7 illustrates a flowchart depiction an alternative embodiment of a method of performing the lead condition assessment.

Turning now to FIG. 7, a flowchart depiction of an alternative illustrative embodiment of performing the lead condition assessment is provided. The IMD 200 may receive a command to perform a lead condition assessment (block 710). The command to perform the lead condition assessment may come from an external source or from an internal source (e.g., the controller 310). Alternatively, the IMD 200 may be programmed to generate a signal to initiate the lead condition assessment process, e.g., at a regular interval such as a day, a week, or a month. Upon initiation of the lead condition assessment test, the IMD 200 may measure the first impedance 240, which may be between the first electrode 220 and a reference electrode (block 720). The measurement of the first impedance 240 may include delivering a signal, such as a test pulse signal, to the first electrode. The IMD 200 measures the resultant voltage in response to the current test signal delivered to the electrode 220.

Upon receiving the command to perform the lead condition assessment, the IMD 200 may also measure the signal artifact on the second electrode (i.e., a first signal artifact) resulting from the test signal sent to the first electrode (block 730). The signal artifact data may then be stored for further analysis. The IMD 200 may also perform a measurement of the second impedance (block 740). While delivering a test signal to perform the measurement of the second impedance, the resultant signal artifact on the first electrode (i.e., a second signal artifact) is also measured (block 750). The IMD 200 may then perform an analysis of the differences in the signal artifact on the first electrode and the second electrode (block 760). Various characteristics, such as the amplitude, the pulse width, etc., relating to the first and second signal artifacts may be analyzed.

Upon analysis of the signal artifacts, the IMD 200 may make a determination whether the difference between the first and the second signal artifacts (i.e., an artifact differential) is above or below a predetermined threshold/tolerance range (block 770). Upon a determination that the difference between the first and the second signal artifacts is within the tolerance range, a report that no significant condition errors are detected may be provided by the IMD 200 (block 780). Upon a detection that the differences between the first and the second signal artifacts are outside the tolerance range, the IMD 200 may provide an indication that the electrodes and/or the corresponding lead conditions are suspect (block 790). Therefore, the impedance measurements and/or the signal artifacts resulting from energizing the electrodes may be used to determine and assess the possible lead conditions. In an alternative embodiment, the impedance measurements of FIG. 6, as well as the signal artifact measurements of FIG. 7, may be combined to provide further indications of possible lead condition errors and their possible causes.

Figure 8:
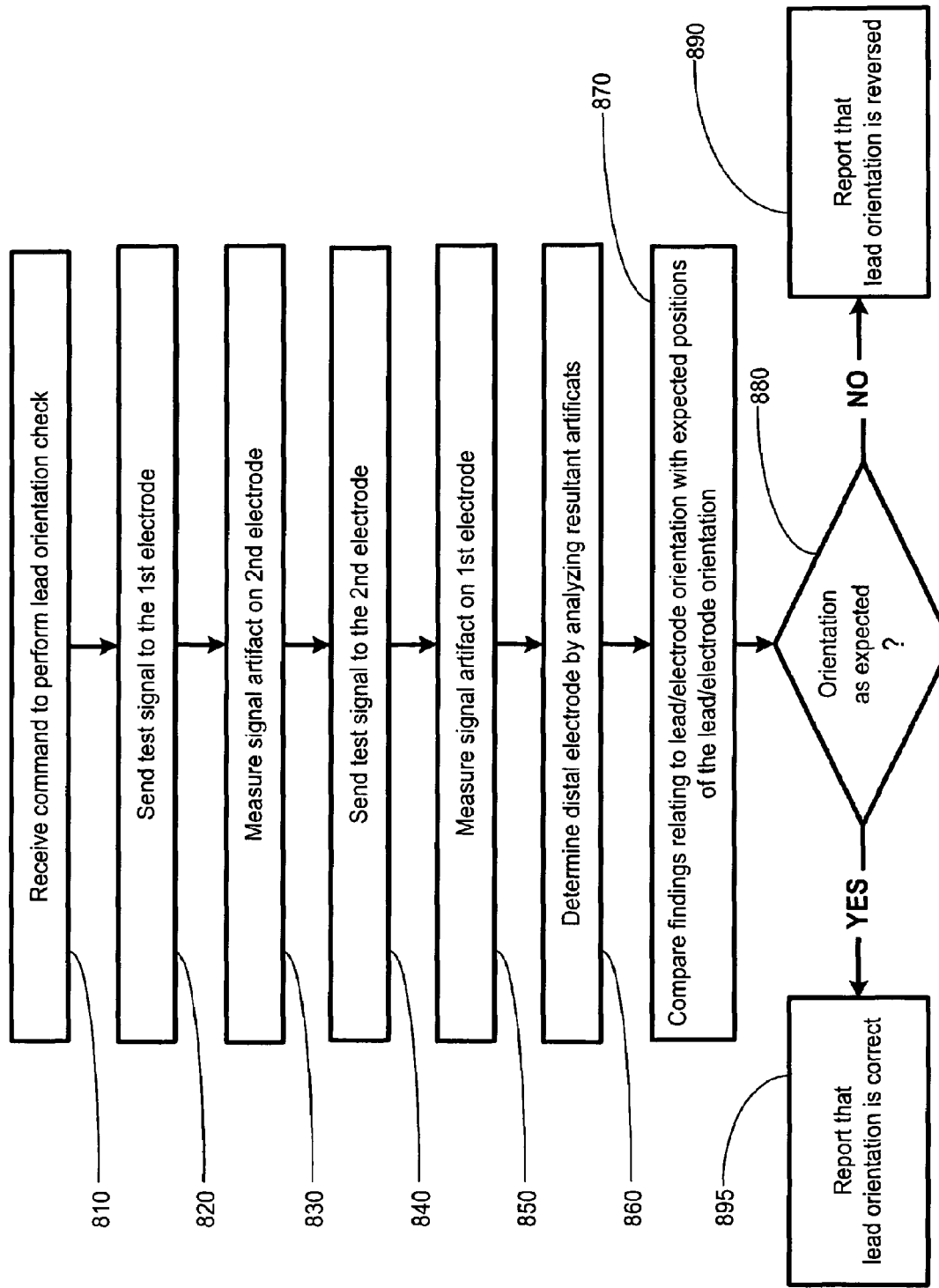
FIG. 8 provides a flowchart depiction of the method of performing a lead orientation detection, in accordance with one illustrative embodiment of the present invention.

Turning now to FIG. 8, a flowchart depiction of performing the lead orientation detection, in accordance with an illustrated embodiment of the present invention is illustrated. The IMD 200 may receive a command to perform a lead orientation check or assessment (block 810). This command may be received from an external source via the communication unit 360. Alternatively, the command to perform the lead orientation check may be an automated self-check that may be performed in an automated pre-determined fashion and/or may be resultant of a pre-determined triggering of a condition. Upon receiving the command to perform the lead orientation check, the IMD 200 may provide a signal, such as a current pulse signal, to the first electrode (block 820). The pulse signal may be similar to the test signal described above. Upon sending the pulse signal to the first electrode, a resultant signal artifact on the second electrode may be measured (block 830). The signal artifact may then be recorded for further analysis (block 830).

Additionally, the IMD 200 may send a test signal to the second electrode 230 (block 840). Based upon the signal sent to the second electrode 230, the IMD 200 may measure a resultant artifact on the first electrode (block 850). This data may also then be stored for further analysis. Based upon the artifact signals detected on the first and the second electrodes, the IMD 200 may identify the distal electrode as well as the proximal electrode by (block 860). For example, the distal electrode may provide a larger signal artifact on the proximal electrode as compared to the artifact signal produced on the distal electrode as a resultant of the signal energized on the proximal electrode. The first electrode 220, which is a proximal electrode being energized by a test signal, may provoke a smaller artifact signal on the second/distal electrode 230. Conversely, the distal electrode (the second electrode 230) being energized by a test signal may produce a larger artifact signal on the proximal first electrode 220. This may be true since the current flow during each test signal pulse may be directed towards the IMD 200. Therefore, an electrode that is between the distal electrode and the IMD 200, i.e., the proximal electrode (first electrode 220) may experience a larger artifact due to the current flow flowing through it.

Based on the similar reasoning, the distal electrode, i.e., the second electrode 230 may produce a smaller artifact due to the fact that much of the current resultant from the energizing of the proximal electrode (the first electrode 220) flows towards the IMD 200, away from the distal electrode 230. Therefore, the artifact level on the second electrode 230 (i.e., the distal electrode) may be smaller. Therefore, the signal artifact level comparisons may be used to identify the proximal electrode and the distal electrode. These findings may be then compared with the expected indication of which electrode is the distal electrode and which electrode is the proximal electrode (block 870).

A determination is made whether the orientation that is predetermined is equivalent to the measured distal and proximal positions of the electrodes (block 880). Upon a determination that the lead orientation is different from the pre-determined lead orientation, the IMD 200 may report that the lead/electrode orientation may have been reversed (block 890). Upon a determination that the measured lead orientation is the same as the expected lead orientation, a report by the IMD 200 may be provided indicating that the lead orientation is correct (block 895). In this manner, the IMD 200 is capable of automatically detecting and reporting whether the lead orientation has been inadvertently or intentionally reversed. This information may then be sent to an external entity, such as a physician, via the communication unit 360. The physician may then take corrective action. Alternatively, the physician may not react based on various reasons, such as the fact that the resulting benefits from treatments made to date may have been satisfactory. Accordingly, an automated check may be performed to warn a physician that lead orientation, as originally intended, may have been reversed.

Figure 9:
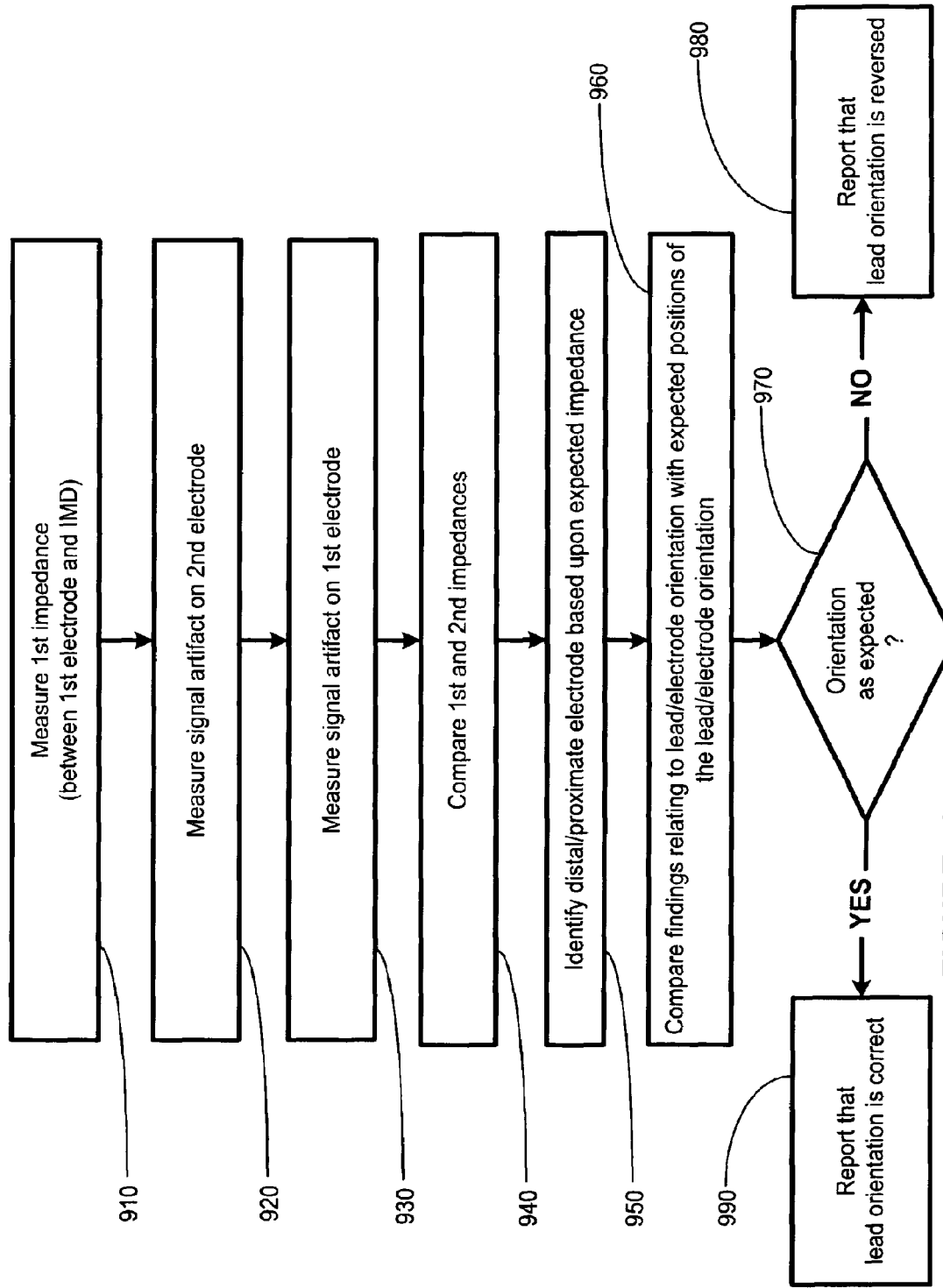
FIG. 9 provides flowchart depiction of an alternative embodiment of a method of performing the lead orientation detection.

Turning now to FIG. 9, an alternative embodiment of performing the lead orientation detection in accordance with an alternative embodiment of the present invention is illustrated. The IMD 200 may receive a command to perform a lead orientation check (block 910). Upon initiation of the lead orientation check, the IMD 200 may measure the first impedance 240, which may be between the first electrode 220 and a reference electrode (block 920). The measurement of the first impedance 240 may entail delivering a signal, such as a test pulse signal, to the first electrode. The IMD 200 measures the resultant voltage in response to the current test signal delivered to the electrode 220. The IMD 200 may also perform a measurement of the second impedance (block 930). The IMD 200 may then perform a comparison between the first and the second impedances (block 940). Based on the impedances comparison the IMD 200 may identify the distal/proximal electrode in light of the expected impedance (block 950). This may be based upon a reasoning that the distal electrode impedance may be higher than the impedance relating to the proximal electrode impedance due to various reasons, such as lead length due to additional distance of the distal electrode, intermediate tissue impedance, etc. Therefore, utilizing impedance measurements and comparisons, an indication relating to the identification and the position of the distal/proximal electrodes/leads may be performed (block 960).

A determination is made whether the orientation that is predetermined is equivalent to the measured distal and proximal positions of the electrodes (block 970). Upon a determination that the lead orientation is different from the pre-determined lead orientation, the IMD 200 may report that the lead/electrode orientation may have been reversed (block 980). Upon a determination that the measured lead orientation is the same as the expected lead orientation, a report by the IMD 200 may be provided indicating that the lead orientation is correct (block 990). In this manner, the IMD 200 is capable of automatically detecting and reporting whether the lead orientation has been inadvertently or intentionally reversed. This information may then be sent to an external entity, such as a physician, via the communication unit 360. The physician may then make corrective actions. Alternatively, the physician may not react based on various reasons, such as the fact that the resulting benefits from treatments made to date may have been satisfactory. Using this technique, an automated check may be performed to warn a physician that lead orientation, as originally intended, may have been reversed.

Utilizing embodiments of the present invention, automated lead orientation detection and/or lead assessments may be performed. The IMD 200 may perform these checks based on external signals, internal pre-determined timing signals, triggering of various events, etc. Based upon the lead assessments and/or the lead orientation, corrective actions may be performed and/or adjustments to the operation of the IMD 200 may result.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A method for assessing a condition of a lead assembly coupled to an implantable medical device (IMD), the method comprising:
    determining by an impedance unit of the IMD or an external unit in communication with the IMD a first impedance relative to a first electrode and a reference electrode;
    determining by the impedance unit of the IMD or the external unit in communication with the IMD a second impedance relative to a second electrode and the reference electrode;
    comparing by the impedance unit of the IMD or the external unit in communication with the IMD the first impedance to the second impedance to determine an impedance difference;
    determining by the impedance unit of the IMD or the external unit in communication with the IMD a position of the first electrode relative to the second electrode based on at least the impedance difference;
    determining a third impedance, the third impedance comprising the impedance relative to the first electrode and the second electrode;

determining whether the impedance difference is outside a predetermined tolerance range;

comparing the impedance difference to the third impedance; and identifying a source of a lead condition error based upon the comparing of the impedance difference to the third impedance, the source comprising at least one of the first electrode, the second electrode, and a physiological impedance.

2. The method of claim 1, wherein the reference electrode comprises a portion of the IMD.

3. The method of claim 1, wherein the first electrode is an EEG sensing electrode.

4. The method of claim 1, further comprising receiving at the IMD a signal prompt from an external source to initiate assessment of a condition of the lead assembly.

5. The method of claim 1, further comprising:
providing an indication of the lead condition error in response to determining that the impedance difference is outside a predetermined tolerance range to a memory of the IMD or a communication unit of the IMD.

6. The method of claim 1, wherein determining the first impedance comprises:
providing a test current signal from the IMD to the first electrode;
measuring a voltage signal across the first electrode and the reference electrode, the voltage signal resulting from the test current signal; and
determining the first impedance based upon the test current signal and the voltage signal.

7. The method of claim 1, wherein determining the second impedance comprises:
providing a test current signal from the IMD to the second electrode;
measuring a voltage signal across the second electrode and the reference electrode, the voltage signal resulting from the test current signal; and
determining the second impedance based upon the test current signal and the voltage signal.

8. The method of claim 1, further comprising:
measuring a first signal artifact relating to the second electrode, the first signal artifact resulting from a test current signal being applied to the first electrode;
measuring a second signal artifact relating to the first electrode, the second signal artifact resulting from a test current signal being applied to the second electrode; and
comparing the first signal artifact to the second signal artifact to determine a signal artifact differential;
wherein determining the position of the first electrode relative to the second electrode is further based on the signal artifact differential.

9. The method of claim 8, further comprising determining which of the first electrode and the second electrodes is positioned distal to the reference electrode based upon the signal artifact differential.

10. The method of claim 1, further comprising determining which of the first electrode and the second electrode is positioned distal to the reference electrode based upon the comparing of the first impedance to the second impedance.

11. The method of claim 10, wherein determining which of the first electrode and the second electrode is positioned distal to the reference electrode comprises determining whether the first impedance is greater than the second impedance.

12. The method of claim 10, wherein determining which of the first electrode and the second electrode is positioned distal to the reference electrode comprises determining whether the positioning of the first and second electrodes is the reverse of an expected positioning.

13. The method of claim 1, wherein the second electrode is an EEG sensing electrode.

14. The method of claim 1, wherein the position of the first electrode is distal or proximal to the reference electrode.

15. The method of claim 1, wherein steps of the method are performed by a processor executing instructions stored on a computer-readable storage device.

16. A method for determining a condition of a lead assembly associated with an implantable medical device (IMD) using an impedance unit of the IMD or an external unit in communication with the IMD, the method comprising:
providing a first test signal from the IMD to a first electrode coupled to the IMD through a first lead;
measuring a first signal artifact relating to a second electrode coupled to the IMD through a second lead, the first signal artifact resulting from the first test signal being applied to the first electrode;
providing a second test signal from the IMD to the second electrode;
measuring a second signal artifact relating to the first electrode, the second signal artifact resulting from the second test signal being applied to the second electrode;
comparing the first signal artifact to the second signal artifact to determine a signal artifact differential;
determining whether the signal artifact differential is outside a predetermined tolerance range; and
providing an indication of a lead condition error in response to determining that the signal artifact differential is outside the predetermined tolerance range to a memory of the IMD or a communication unit of the IMD.

17. The method of claim 16, further comprising determining whether the signal artifact differential relates to at least one of a resistive characteristic, an inductive characteristic and a capacitive characteristic to determine whether the source of the lead condition error relates to at least one of the first electrode, the second electrode, and a physiological impedance.

18. An implantable medical device (IMD) comprising:
a stimulation unit configured to deliver an electrical signal to a patient, wherein the stimulation unit is configured to be coupled to a first electrode, wherein the stimulation unit is configured to be coupled to a second electrode;
an impedance unit configured to determine a first impedance between the first electrode and a reference electrode, wherein the impedance unit is configured to determine a second impedance between the second electrode and the reference electrode, wherein the impedance unit is configured to compare the first impedance to the second impedance to determine an impedance difference;
a processor coupled to the impedance unit and configured to determine a position of the first electrode relative to the second electrode based on at least the impedance difference; and
the impedance unit is further configured to determine a third impedance between the first electrode and the second electrode and to compare the impedance difference to the third impedance, wherein the processor is further configured to identify a source of lead condition error based on the comparison of the impedance difference to the third impedance, the source comprising at least one of the first electrode, the second electrode, and a physiological impedance.

19. The IMD of claim 18, wherein the first electrode is an EEG sensing electrode.

20. The IMD of claim 18, wherein the second electrode is an EEG sensing electrode.

* * * * *